(12) United States Patent
Palestro et al.

(10) Patent No.: US 6,264,888 B1
(45) Date of Patent: Jul. 24, 2001

(54) ULTRAVIOLET GERMICIDAL APPARATUS AND METHOD

(75) Inventors: Richard P. Palestro; Dale R. Morgan, both of Aurora; Michael Dee Iseman, Englewood; Donald Preston Rosier, Arvada, all of CO (US)

(73) Assignee: National Jewish Center for Immunology and Respiratory Medicine, Denver, CO (US)

( * ) Notice: Subject to any disclaimer, the term of this patent is extended or adjusted under 35 U.S.C. 154(b) by 0 days.

(21) Appl. No.: 08/293,153

(22) Filed: Aug. 18, 1994

Related U.S. Application Data

(63) Continuation of application No. 08/087,178, filed on Jul. 2, 1993, now abandoned, which is a continuation-in-part of application No. 07/960,085, filed on Oct. 9, 1992, now abandoned.

(51) Int. Cl.[7] ......................................................... A61L 2/10
(52) U.S. Cl. ................................................................ 422/24
(58) Field of Search ................................................. 422/24

(56) References Cited

U.S. PATENT DOCUMENTS 3,073,978 * 1/1963 Minto .
3,757,495 * 9/1973 Sievers ..................................... 55/316
5,074,894 * 12/1991 Nelson .................................... 55/210

* cited by examiner

Primary Examiner—Timothy McMahon
(74) Attorney, Agent, or Firm—Gibson, Dunn & Crutcher LLP

(57) ABSTRACT

A germicidal method and apparatus for destroying airborne pathogenic bacteria such as tuberculosis bacteria using ultraviolet light. Air is drawn through a filter and into a sterilization chamber that is irradiated with ultraviolet light, and out through an exhaust opening. Consideration for the characteristics of the room in which the apparatus is installed and the positioning of the installation allows effective prevention of transmission of disease through expectoration and inhalation of airborne microdroplets of bacteria-containing sputum. The filter is of the low-density type which traps large particulates, but not small particulates of the size of the microdroplets, so that the filter does not become a bacteria colonization site. Baffles on the air intake opening and air exhaust opening to prevent ultraviolet light from escaping into the environment. The sterilization chamber is constructed such that the air passes the ultraviolet light bulbs twice as it circulates therethrough.

9 Claims, 1 Drawing Sheet

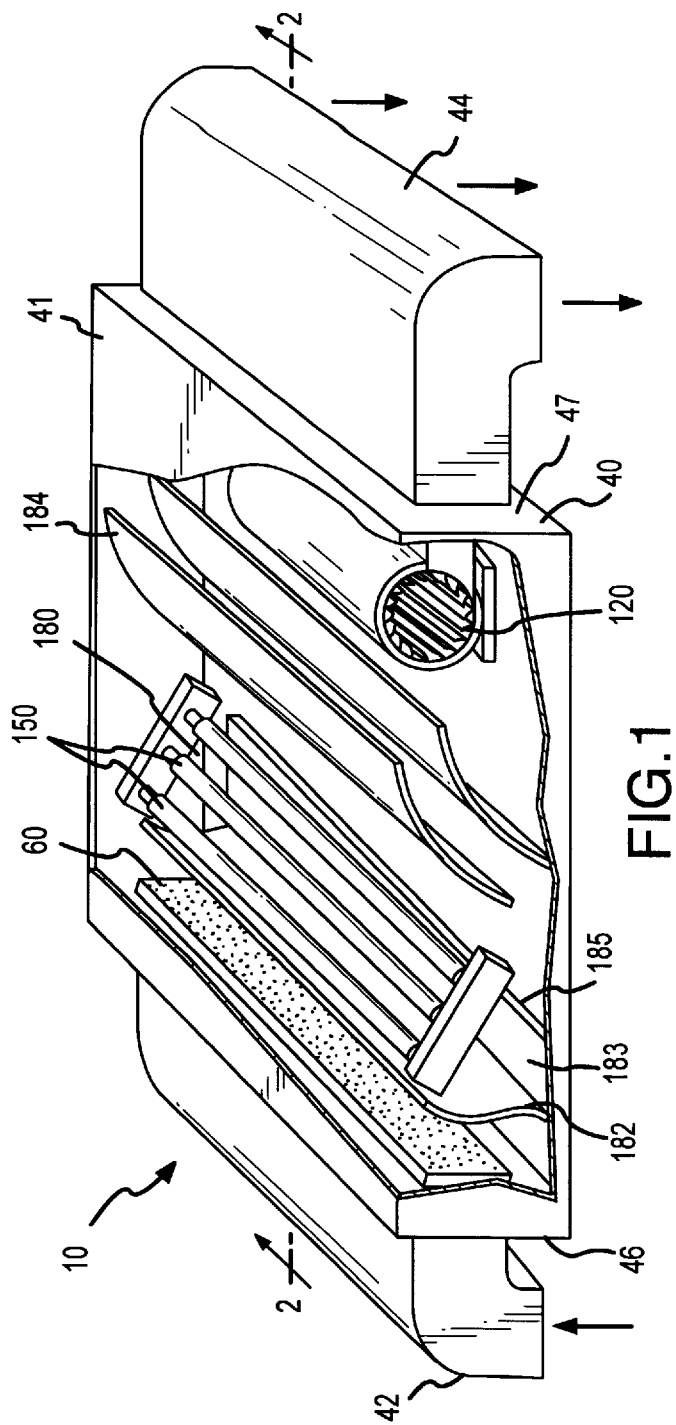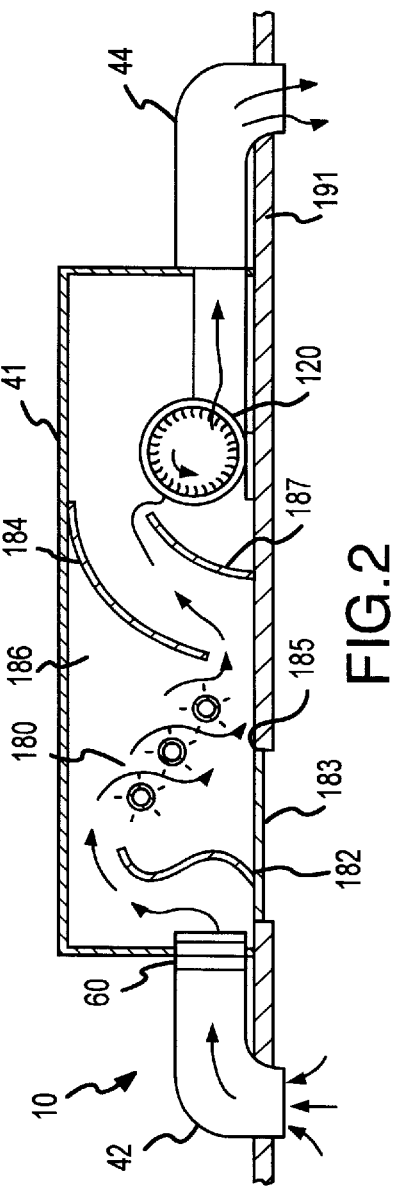

ULTRAVIOLET GERMICIDAL APPARATUS AND METHOD

This is a continuation of application Ser. No. 08/087,178 filed Jul. 2, 1993, now abandoned which is a continuation-in-part of application Ser. No. 07/960,085 filed Oct. 9, 1992 now abandoned.

FIELD OF THE INVENTION

The present invention relates to the field of germicidal systems employing bacteria-destroying ultraviolet lights. In particular, the present invention relates to a system for producing an air flow through a baffled ultraviolet sterilization chamber mounted behind a wall or ceiling, wherein the ultraviolet light intensity, the air residency time, and the air exchange rate for the air volume in a given space, are such that a percentage of tuberculosis bacteria are destroyed that effectively prevents transmission of such disease by airborne sputum.

BACKGROUND OF THE INVENTION

Tuberculosis is the most common cause of death from infectious disease in the world today. It infects millions of people each year and causes hundreds of thousands of fatalities. The disease is particularly prevalent in less-industrialized countries where high population densities, poor sanitary conditions and a high percentage of individuals in poor health contribute to the spread of infectious diseases.

After a long period of declining rates of tuberculosis infection in the United Sates, it is believed that the infection rate is now increasing. The increasing rate is apparently due to a combination of factors. One factor is undoubtedly increased immigration from parts of the world with high rates of infection. For example, in the United States the case rate of tuberculosis per 100,000 population was 9.3 in 1985, resulting in over 22,000 cases and over 1,200 deaths. In Southeast Asia, both the case rate and the death rate are believed to be many times that, and immigrants from that part of the world now constitute 3 to 5% of new cases in the United States.

Another factor related to increased rates of tuberculosis infection appears to be the use of living quarters with high population densities and less-than-ideal sanitary conditions for persons in ill health who are susceptible to the disease. Such conditions are commonly found in shelters for the homeless, prisons and some nursing homes. Another important factor in the increased rate of infection is infections among patients with Acquired Immune Deficiency Syndrome (AIDS) and intravenous drug users.

Another reason for the recent increased incidence of tuberculosis is probably the failure of many medical professionals to diagnose and treat the disease early and properly. The relative rareness of the disease in the United States since the early epidemics resulted in an entire generation of health care workers without much experience in the disease. Further, diagnosing the disease is not always easy, for the symptoms are similar to the symptoms of many other disorders. Therefore, the disease is often misdiagnosed and mistreated, and the degree of infectiousness of the disease is underappreciated.

Even after it is recognized that a set of symptoms may indicate tuberculosis, the tests for the disease are somewhat imprecise and tend to require judgment by an experienced professional. For example, one diagnostic tool is chest x-rays which typically show apical-posterior segment cavitary changes in tuberculosis infected patients. However, in elderly individuals—who comprise a relatively large proportion of tuberculosis patients—lobar or patchy lower-zone shadows may simulate bacterial or aspiration pneumonia. Also, x-rays in the elderly may mislead the physician by showing a solitary pulmonary nodule or a pleural effusion. Another important tuberculosis test is the tuberculosis skin test, but a major disadvantage to the tuberculosis skin test is that it generates a high number of both false-positive and false-negative results. The most precise test is microscopic examination of a sputum sample, but this test may require the use of at least three separate samples of sufficient volume, which may require gastric aspiration or bronchoscopy in patients with low sputum production.

The normal body reaction to infection by tuberculosis bacteria is to build a fibrous wall around each bacterium. Initially, a person may be unaware of any infection, but over a period of months or even years the infection produces inflammation and eventually destruction of tissue. The manifestations as the disease progresses generally include cough, fever, night sweats, hemoptysis, chest pain, weight loss and malaise. The usual treatment for tuberculosis is administration of drugs over a period of many months such as isoniazid, rifampin and pyrazinamide and ethambutol. Persons recently infected but with no active disease are usually given isoniazid preventive therapy, particularly if they have other risks such as malnutrition, gastrectomy, diabetes mellitus, pneumoconiosis, malignancy or if for some reason they have immunosuppression such as from corticosteroid therapy, renal impairment or HIV infection. In short, tuberculosis in a normal healthy patient is typically a disease that is curable by drugs, although the drug therapy is quite prolonged. A serious concern—and yet another reason for the recent increase in tuberculosis—is the development of drug-resistant tuberculosis. It is estimated that at least 5% of new cases are resistant to the usual drug therapy, and that the percentage in some areas of the United States is as high as 20%. While non-drug-resistant tuberculosis is typically 99% curable in patients with normal immune responses, drug-resistant tuberculosis is only about 50–60% curable. A related concern is drug therapy on non-drug-resistant tuberculosis for patients who are intolerant of the drugs. In those cases, drug therapy is complicated because the drug is effective against the infection but has serious adverse effects on the patient such as hepatitis or serious rashes.

Another concern is raised by the increasing incidence of non-tuberculosis mycobacterial pulmonary infections. Many such infections produce symptoms similar to those of tuberculosis infections, but may be more difficult to identify and treat. Moreover, they may be transmitted through the same means as tuberculosis and tend to infect the same types of susceptible individuals.

The transmission of the tuberculosis bacteria is accomplished almost exclusively by infected individuals expectorating microdroplets of bacteria-containing sputum by coughing or sneezing. These microdroplets are suspended in the air and are inhaled by other individuals in the vicinity. The bacteria typically lodges in the lower lung where it proliferates, and may be disseminated to other organs as well. The microdroplets of sputum which contain the bacteria may be very small—on the order of 0.01 microns. In fact, it appears that the smallest droplets are the most effective in communicating the disease since the smallest droplets stay airborne indefinitely and are easily inhaled to the lower lung where they are not readily removed. Studies have shown that aerosol droplets on the order of 1–5 microns are highly effective vehicles for transmitting the disease.

One controversial approach to combatting the disease has been the use of vaccines. However, the efficacy of tuberculosis vaccines is debatable. Even the trials which seemed to show some efficacy have shown less efficacy among adults than among infants and children. An additional objection to widespread vaccinations is that by inducing tuberculin reactivity in the population they would confound the detection and measurement of infections through the use of skin tests, since skin tests in vaccinated individuals would presumably result in a false-positive. This would severely curtail the practice of preventive drug therapy among infected patients who have not yet developed outward symptoms.

The airborne aspect of the disease has led toward systems for preventing the transmission of the disease which focus on filtration and sterilizing devices. One approach is the use of masks. Simple surgical masks are thought to be insufficient in view of the very small size of the sputum microdroplets which are effective in communicating the bacteria. Instead, disposable particulate respirators are recommended. The use of masks is fraught with practical difficulties; they are physically uncomfortable, they impair breathing (which is already impaired for many patients), and they disrupt speaking. To be effective at all, it would probably be necessary for the masks to be worn not just by the patients, but also by noninfected individuals. In view of the long distances that airborne microdroplets containing viable bacteria can travel, it would be necessary for the masks to be worn by noninfected individuals throughout the general vicinity of a patient and not just those in the immediate presence of a patient. Moreover, it is not known for certain whether the use of masks would actually be effective even if the practical problems were tolerated or overcome.

Another preventive measure which relies on the airborne aspect of the bacteria is the use of modified ventilation systems. It is currently recommended that facilities used for tuberculosis patients undergo certain minimum air exchange rates, under the theory that dilution of infectious air with clean air will reduce the concentration of bacteria and hence the likelihood of transmission of the disease. While this approach is theoretically sound, it is problematic in implementation. Modern buildings are normally designed with fixed ventilation systems which are not easily modified to produce the requisite air exchange rate. Even if they are suitably modified, they may be rendered ineffective by an open door or by shifting air-flow patterns. A high air exchange rate also increases cooling and heating costs. Finally, there is the issue of the ultimate disposition of the contaminated air that is removed, and whether it is appropriate to simply release it outside the facility.

Another approach to reducing the transmission of the disease is the use of high-efficiency filtration systems. For such a system to be effective, however, it must employ a very dense filter to trap very small particles. This entails a powerful fan, high energy usage, loud noise, and meticulous installation and maintenance. There is also concern that the filters and the rest of the air-flow path may themselves become sites of bacteria colonization.

Yet another approach to reducing the transmission of the tuberculosis bacterial employs ultraviolet light as a germicide. It was discovered some time ago that airborne bacteria are susceptible to ultraviolet light in wavelengths of about 254 nm. Wells S. F., *On Air-Borne Infection: II-Droplets and Droplet Nuclei*, Am. J. Hyg. 1934 20: 611–8; Wells W. F., Fair G. M., *Viability of E. Coli Exposed to Ultraviolet Radiation in Air*, Science 1935; 82:280–1. That finding led to the development of systems using ultraviolet light as a germicide against airborne bacteria such as measles and tuberculosis. However, interest in such systems diminished when later investigators were unable to obtain the desired efficacy. Also contributing to the diminished interest in such systems was the recognition that ultraviolet lights produced harmful ozone and also produced skin and eye irritation. With the development of streptomycin and chemotherapy for tuberculosis treatment, the belief became prevalent that tuberculosis would be eradicated and that preventive systems would be unnecessary.

The systems that were developed using ultraviolet light as a germicide against tuberculosis were imprecise, marginally effective, and perhaps dangerous. The most common system simply employed ultraviolet lights mounted on or suspended from a wall or ceiling of a room. For example, a system employing lights suspended from the ceiling is described in some detail in Riley, R. Z., Knight, M. and Middlebrook, G., *Ultraviolet Susceptibility of BCG and Virulor Tubercle Bacilli*, Am. Rev. of Resp. Dis., 1976, 113:413. The problems in such a system are numerous. It relies completely on normal air circulation in the room where it is installed to bring the bacteria within range of the ultraviolet light. The normal circulation in a room may be too low for the ultraviolet light to destroy a necessary proportion of bacteria, or the normal circulation may be high enough but of a pattern that does not bring the airflow past the ultraviolet light. Moreover, there is no single test to determine whether the circulation rate and patterns are adequate or not for a given installation. Further, such systems quickly become contaminated by dust on the light bulbs which diminishes their effectiveness. From a safety standpoint, one of the greatest concerns is that the simple light shields used with such systems allow light to be reflected off the walls and ceiling and onto the skin and eyes of the occupants. The degree of danger associated with the indirect ultraviolet irradiation is disputed, but there is undoubtedly at least some danger if the period of exposure is prolonged. In explaining the necessary safety precautions, Riley, R. L. and Nordell, E. A., *Clearing the Air, The Theory and Application of Ultraviolet Air Disinfection*, Am. Rev. Respir. Dis. 1989 139:1286, stated:

> Does germicide UV cause inflammation of skin and eyes? It can, but the standard set by the National Institute of Occupational Safety and Health (NIOSH) is very conservative. Overhead installations must be inspected for 'hot spots' (greater than 0.2 uW/cm$^2$) with a sensitive UV meter. Installers should anticipate readjusting fixture height up or down based on meter readings. Baffles designed to prevent direct eye contact will also need adjustment after the initial installation. Excessively reflective surfaces about fixtures may contribute to excess radiation, but this can be reduced with nonreflective paint or by spraying the surface with stove black. If the intensity of UV does not exceed 0.2 uW/cm$^2$, the likelihood of skin or eye irritation is minimal during an 8-h exposure. Persons with especially sensitive skin, with systemic lupus erythematous, for example, may need to avoid exposure or take measures to protect their skin.

This illustrates some of the difficulties and dangers of employing ultraviolet lights behind a simple light shield; the light may generate dangerous and unpredictable "hot spots", it is not appropriate for those with sensitive skin or eyes, and it requires careful consideration of the placement and the orientation and reflectivity of the surrounding surfaces. Finally, even if all those precautions are observed, the quote only indicates that skin and eye irritation is "minimal" rather than nonexistent and only for exposure periods of 8 hours.

Of course, for the system to be effective against transmission of airborne disease in, for example, a patient room, it would have to operate continuously and not just for 8 hour periods. The article goes on to acknowledge that:

> UV or disinfection that is inappropriately applied, poorly planned, or carelessly used may be ineffective, dangerous, and falsely reassuring. The guidelines and precautions listed above are not intended to enable a would-be user of UV to plan, purchase, install, or check the adequacy of a UV installation. Detailed instructions for UV installers have been published. However, there is currently little commercial interest in UV for air disinfection and, therefore, little expert guidance for comprehensive planning and installation. Renewed consumer interest may stimulate the UV industry to correct this deficiency.

Notwithstanding the uncertainly expressed in the Riley and Nordell article regarding the dangers of ultraviolet radiation, that article is actually more cognizant of those dangers than much of the other literature on the subject. For example, the article by Riley, Knight and Middlebrook, supra, does not even mention the dangers to the skin and eyes of ultraviolet radiation, or any precautions that should be taken to minimize those dangers.

There are number of ultraviolet germicidal systems that have been patented, but as in the case of the scientific literature mentioned above, those patents teach little about the dangers of ultraviolet radiation and how to effectively minimize the dangers, or how to position and operate the devices to achieve the requisite bacterial kill rate to prevent transmission of disease.

For example, U.S. Pat. No. 3,975,790 by Patterson is for an ultraviolet lamp fixture used in combination with a conventional commercial vacuum cleaner, and U.S. Pat. No. 4,087,925 by Bienek is for a sterilizing hand dryer, in which ultraviolet lights are positioned within the housing of a blower that is used to dry wet hands, where the blower is of the type commonly used in commercial restrooms. The devices of Patterson and Bienek seem to include little or nothing for light baffling to prevent leakage of allowable light to outside the housing, and the patents teach nothing about optimal flow rates, air-exchange rates or other information for the effective use of the machines. The devices are obviously intended as general, and only partially effective, sterilizing tools rather than as comprehensive and predictably effective systems.

Another patent, U.S. Pat. No. 4,210,429 by Golstein, employs a "squirrel-cage" type blower which draws air into a housing through a air intake filter, through the blower, and through a sterilization chamber containing ultraviolet lights. The air leaves the sterilization chamber, passes through a second filter and a charcoal filter and finally exits through an outlet. The specification indicates that the purpose of the device is to remove "pollens, lung damaging dust, smoke, bacteria and any one of a number of other irritants and micro-organisms" and that it does so for "particles down to 0.3 microns in size with an efficiency of 99.9%". The device is characterized as an "air purifier" rather than as a germicidal device; the use of three distinct filters including a very fine filter for removing extremely small particles, a charcoal filter for removing odors and a pre-filter for removing particles, is distinguishable in design and function from the present invention. This extensive filtration would require a high-capacity blower to achieve any effective air exchange rate. The device is not specifically designed for destroying the tuberculosis bacteria or any other specific bacteria, although it would obviously be effective in doing so to some extent. Therefore, the patent teaches nothing about the use of the device for that purpose or the optimal flow rates or positioning of the device for that purpose.

U.S. Pat. No. 5,074,894 by Nelson is for a hospital room to quarantine patients with tuberculosis or other respiratory diseases caused by airborne pathogens. Although one embodiment of the system includes an air circulation circuit with ultraviolet lights, the patent is directed primarily toward negative pressure and filtering aspects utilizing high-efficiency particulate air filters.

Other patents describing the use of ultraviolet light as a germicide against airborne bacteria include, U.S. Pat. No. 4,448,750 by Fuesting, U.S. Pat. No. 4,896,042 by Humphreys, U.S. Pat. No. 4,990,311 by Hirai and U.S. Pat. No. 4,047,072 by Wertz, U.S. Pat. No. 4,990,313 by Pacosz, U.S. Pat. No. 3,072,978 by Minto, U.S. Pat. No. 4,227,446 by Sore, U.S. Pat. No. 3,347,0235 by Wiley, U.S. Pat. No. 4,786,812 by Humphreys, U.S. Pat. No. 4,990,311 by Hirai, U.S. Pat. No. 4,931,654 by Horng, U.S. Pat. No. 4,806,768 by Keutenedjian, U.S. Pat. No. 4,750,917 by Fugii, U.S. Pat. No. 3,757,495 by Sievers, U.S. Pat. No. 3,750,370 by Brauss, U.S. Pat. No. 3,745,750 by Arff, U.S. Pat. No. 3,744,216 by Halloran, U.S. Pat. No. 3,674,421 by Decupper, U.S. Pat. No. 3,576,593 by Cicirello, and U.S. Pat. No. 5,185,015 by Searle. Patents directed toward the use of ultraviolet light as a germicide against bacteria in water or other liquids include U.S. Pat. No. 4,400,270 by Hillman, U.S. Pat. No. 4,482,809 by Maarschalkerweerk, U.S. Pat. No. 5,102,450 by Stanley and U.S. Pat. No. 5,124,131 by Wekhof.

SUMMARY OF THE INVENTION

The present invention is an apparatus and process for destroying airborne pathogenic bacteria such as the tuberculosis bacteria. Ultraviolet lights of a sufficient intensity are positioned within a sterilization chamber where they irradiate an air stream containing the bacteria, typically in the form of suspended microdroplets of sputum. The sterilization chamber has an exit and an entrance, and a blower is positioned preferably at the exit to draw air into the entrance and through the sterilization chamber and out the exit. The air circulates behind an intake baffle and into the sterilization chamber having a set of ultraviolet lights. An outlet baffle at the opposite side of the sterilization chamber bounces the air that passes the ultraviolet lights back over the ultraviolet lights a second time, and around the outlet baffle to the fan. The fan then expels the sterilized air back into the room. The air passing through the sterilization chamber is virtually completely sterilized of viable tuberculosis bacteria by the chosen dosimetry of the system, which is achieved by appropriately sizing the sterilization chamber employing ultraviolet lights of the correct intensity, and utilizing the right air flow rate through the blower. The apparatus is configured to fit behind a wall in a room, or preferably, above a suspended ceiling. Air is drawn by a fan from the room into an intake duct and into the apparatus.

The sterilization chamber includes a filter on the intake side to filter out large particles such as dust, in order to minimize the contamination of the ultraviolet light bulbs. The filter is deliberately designed not to intercept small particles such as microdroplets, since the filter could then become a bacteria colony. The use of a low density filter also minimizes the resistance to air flow, thereby allowing the use of a smaller, more efficient and quieter blower. With the exception of this intake filter for removing large particulates, the apparatus preferably does not include any devices that would intercept and retain microdroplets or other small particles in a way that resists the air flow and poses the possibility of becoming a bacteria colonization site; the small particulates and microdroplets with destroyed bacteria simply pass through the apparatus and are expelled back into the environment.

Both the air intake and exhaust to the sterilization chamber are baffled so that ultraviolet light must reflect off multiple surfaces before exiting the sterilization chamber. The interior surfaces of the baffles may be light-absorptive to minimize their reflectivity and further lessen the possibility of ultraviolet light leaking from the sterilization chamber into the environment.

The apparatus is used in a space having a volume of air that results in an air exchange rate of preferably 12–15 air exchanges per hour. At that air exchange rate, it has been determined that a sufficient volume of air will circulate through the apparatus and will prevent any air stagnation in the room, that a high enough percentage of tuberculosis bacteria will be destroyed before they are inhaled by persons in the room to prevent transmission of the disease.

BRIEF DESCRIPTION OF THE DRAWINGS

FIG. 1 is a pictorial cutaway view of the present invention.

FIG. 2 is a side sectional view of the present invention, taken along line 2—2 of FIG. 1, installed in a suspended ceiling.

DESCRIPTION OF THE PREFERRED EMBODIMENTS

A pictorial view of a preferred embodiment of the invention is shown in FIG. 1. The principal elements of the invention 10 include an exterior housing 40 having an air intake duct 42 and an air discharge duct 44, a squirrel-cage type blower 120 and set of ultraviolet lights 150 in a sterilization chamber 180 within the housing 40. The air intake duct 42 is preferably positioned at one end 46 of the housing and the air discharge duct 44 is positioned at the opposite end 47 of the housing 40.

As better shown in the sectional view of FIG. 2, the air intake duct 42 has positioned within it a filter 60 which substantially fills the intake duct 42 so that all air drawn through the air intake duct 42 must pass through the filter 60. The filter 60 is preferably not a high-density filter, but is instead designed to intercept and retain only fairly large particulates such as dust. The purpose of the filter 60 is not to allow the apparatus 10 to purify the air, but is merely to intercept dust over 10 microns in size that would otherwise contaminate the ultraviolet light bulbs 150. In a preferred embodiment, the filter is model no. DP1-40, available from Airguard Industries located in Louisville, Kentucky. The filter 60 is retained in the air intake duct 42 by means of clips, brackets or any other suitable retention means (not shown) that allow easy removal and replacement of the filter 60.

It is notable that in the preferred embodiment, there is no filter at all in the air discharge duct 44 or elsewhere downstream from the sterilization chamber. Therefore, the only filter in the preferred embodiment is the large particulate filter 60 positioned in the air intake duct 42. The apparatus 10 is designed to allow small particulates, including microdroplets of sputum containing bacteria that are destroyed by the ultraviolet lights as described below, to be expelled back into the environment. As a result, the apparatus does not have a site that traps and allows the colonization of bacteria, which would require frequent cleaning or sterilization. In addition, there is very little resistance to air flow, thereby allowing the use of a relatively small, low-energy and quiet motor and blower system, as further described below.

In this respect, the present system is fundamentally different from prior art devices that are designed to remove dirt, pollen and other particulates and odor from the air. Those prior art systems employ dense and multiple filters and noisy high-energy blowers to indiscriminately remove impurities from the air. But they are not specifically for the purpose of destroying pathogenic pulmonary bacteria such as tuberculosis and their efficiency in doing so is undocumented and questionable. In contrast, the present system is specifically designed for destroying bacteria such as the tuberculosis bacteria, and is highly effective in accomplishing that using a relatively small, energy efficient, quiet apparatus, but the present system makes no attempt at all to remove impurities from the air. Even the bacteria itself is released back to the environment once it is killed by the apparatus.

The air discharge duct 44 is preferably positioned remotely from the air intake duct 42, so that the exhausted air circulates into the environment rather than being immediately drawn back into the apparatus 10. In the embodiment shown in FIGS. 1 and 2, the positioning of the ducts 42 and 44 on opposite ends of the housing produces a circulatory effect through the environment of the apparatus 10 by drawing air into the apparatus 10 through the air intake duct 42 and expelling air from the apparatus 10 through the air discharge duct 44, roughly in the direction of the arrows shown in FIG. 2. The air discharge duct 44 may be covered with a grill (not shown) to prevent the introduction of hands or objects into the air discharge duct 44 and to diffuse the air stream exhausted from there. A door 183 is positioned in the bottom of the housing 40 as shown in FIG. 2 and is attached to the housing 40 by a hinge 185 or other suitable attachment means. The door is positioned to allow ready access to the ultraviolet lights 150 and to the filter 60 to allow them to be changed or cleaned.

The sterilization chamber 180 is baffled on the upstream side by an intake baffle 182, and on the downstream side by a pair of exhaust baffles 184 and 187, to prevent ultraviolet light from leaking from the sterilization chamber 180 out the air intake duct 42 or air discharge duct 44 and into the environment where it could damage the skin and eyes of patients and other persons. The baffles also improve the circulation of the air over the ultraviolet bulbs in the manner described below. The intake baffle 182 in the preferred embodiment is an S-shaped element fabricated from sheet metal or other appropriate material that is not degraded by ultraviolet light. The lower portion of the intake baffle 182 is curved away from the air intake duct 42 to receive the incoming air, while the upper portion of the intake baffle 182 is curved toward the sterilization chamber 180 to allow the incoming air to flow smoothly over the top of the intake baffle 182 and into the sterilization chamber 180. The intake baffle 182 may be attached to the housing 40 at the bottom of the intake baffle 182 or at the ends.

The exhaust baffles 184 and 187 form a channel therebetween for the air to leave the sterilization chamber 180, as best shown in the sectional view of FIG. 2. Both exhaust baffles 184 and 187 are curved with the inner side of the curve away from the sterilization chamber 180. The air passes under the lower edge of the upper exhaust baffle 184, through the channel defined by the upper baffle 184 and 187, and over the upper edge of the lower exhaust baffle 187.

The upper exhaust baffle 184 may be attached to the housing 40 at the top of the upper exhaust baffle 184 or at the ends. The lower exhaust baffle 187 may be attached to the housing 40 at the bottom of the lower exhaust baffle 187 or at the ends.

It can be appreciated that for any ultraviolet light to escape from the sterilization chamber 180 through the air discharge duct 44, it must reflect off the walls of the sterilization chamber 180, reflect through the channel defined by the upper and lower exhaust baffles 184 and 187, and then through the blower 120 and out the air discharge duct 44. For any ultraviolet light to escape through the air intake duct 42, it must reflect off the walls of the sterilization chamber 180, into the space between the air intake duct 42 and the intake baffle 182, through the air intake filter 60 and through the air intake duct 42. The possibility of light escaping can be further reduced by applying an absorptive coating or paint to the interior surfaces of the baffles 182, 184 and 187 and the other interior surfaces of the housing 40.

Although the baffling described above to prevent ultraviolet light from escaping presents a circuitous route for the passage of air from the air intake duct 42 through the sterilization chamber 180 and out the air discharge duct 44, the baffles are still designed to minimize the resistance to air flow. Thus, as shown by the arrows in FIG. 2, the air can flow reasonably smoothly with limited turbulence loses, thereby allowing a small, quiet and efficient blower system.

An important aspect of the embodiment shown in FIGS. 1 and 2 is that the baffles 182 and 184 and sterilization chamber 180 are configured such that the air passes the ultraviolet lights twice. As shown by the arrows of FIG. 2, the air passes the ultraviolet lights a first time immediately after it passes over the top of the air intake baffle 182 and into the sterilization chamber. The air pathway is blocked on the opposite side of the sterilization chamber by the air exhaust baffle 184. The inclined and curved surface of the air exhaust baffle, together with the top wall of the housing 40, define a space 186 to receive the air after it passes the ultraviolet light a first time. The air then reflects off the air exhaust baffle 184 and out of the space 186 and back toward the ultraviolet lights for a second pass. The air is then drawn out of the sterilization chamber 180 by passing under the exhaust baffle 184 and into the blower 120.

The blower 120 in the preferred embodiment is of the "squirrel-cage" type. The blower 120 draws air through its ends and propels the air out the middle and into the exhaust duct 44. The exact size of the blower and the motor for the blower depend on the desired use of the machine and the size of the environment in which it will be used, as further discussed below. The motor is preferably of the normal alternating current type and is in communication with the electrical system (not shown) of the apparatus, which also powers the ballasts for the ultraviolet lights 152. The electrical system is ordinary, and the details of it will be apparent to those skilled in the wiring of lights and motors, and it is not further described herein.

The apparatus 10 is preferably positioned in the suspended ceiling 191 of a patient room as shown in a preferred arrangement in FIG. 2. Cutouts in the ceiling 191 are provided for the air intake duct 42, air discharge duct 44 and access door 183. The microdroplets from the patient are expectorated from the patient into the surrounding air where they are suspended. The air currents produced by the apparatus 10 draws air into the apparatus 10 from intake duct 42. The filter 60 traps large dust particles, but allows small particles to pass including the micro droplets of small bacteria-containing sputum. The air with the suspended microdroplets passes through the sterilization chamber where the bacteria are destroyed by passing twice over the ultraviolet lights, and the air along with the suspended microdroplets with the then-killed bacteria are expelled from the apparatus 10 back into the room through the air discharge duct 44. Because the air discharge duct 44 is preferably positioned at one end 46 of the apparatus 10 while the air intake duct 42 is positioned at the other end 47 of the apparatus, the air being drawn into the air intake duct 42 and expelled from the air discharge duct 44 produces a circulatory effect through the room which increases the flow of new unsterilized air into the apparatus. This circulatory effect also helps prevent the air from short-circuiting the circulation pattern by leaving the apparatus 10 through the air discharge duct 44 and immediately re-entering the apparatus 10 through the air intake duct 42 without passing through the room.

It has been determined experimentally that transmission of the tuberculosis bacteria from an infected patient to an uninfected person can be effectively prevented by ensuring that there are approximately 10 to 15 air changes per hour in the patient room using the apparatus and positioning described above. The phrase "10 to 15 air changes per hour" means a circulatory effect through the apparatus in which the total volume of air through the apparatus per hour equals the air volume of the room multiplied times a number between 10 and 15, inclusive. For example, one air change per hour in a 1,000 cubic foot room would require an apparatus through which 1,000 cubic feet of air pass per hour. Therefore, in a patient room having dimensions of 10 by 10 by 10 feet for a total volume of 1,000 cubic feet, or other dimensions for a total volume of 1,000 cubic feet, the apparatus should be capable of circulating through it at the rate of 10,000 to 15,000 cubic feet of air per hour.

The exact dimensions of the apparatus to achieve such a flow rate in a preferred embodiment include a housing 40 having a length of about 48 inches, a height of about 15.5 inches, and a depth of about 36 inches. The air intake duct 42 is roughly 6 inches by 24 inches and the air discharge duct 44 is roughly 6 inches by 18 inches. The opening between the top of the air intake baffle 182 and the housing 40 is about 4 inches, and the opening between the bottom of the air exhaust baffle 184 and the housing 40 is about 4 inches. The motor is a 115 volt, 1,725 rpm motor, and the blower 120 includes 4 by 9 inch blower wheels. The ultraviolet lights 152 are model D-36-3 by American U.V. Co.

What is claimed is:

1. A method for destroying airborne tuberculosis bacteria in air in a room having a set of walls and a ceiling panel, comprising mounting a device behind a wall or ceiling panel of the room, filtering the air using a filter mounted on the device, drawing the air through a sterilization chamber in the device having at least one ultraviolet light bulb for irradiating the air with germicidal ultraviolet light such that the air passes the light bulb twice, and releasing the air including destroyed bacteria back into the room.

2. The method of claim 1, wherein the filter traps substantially no particulates and droplets smaller than 10 microns in diameter.

3. The method of claim 1, wherein the device includes an air intake opening for air to enter the device and wherein the filter is positioned between the air intake opening and the sterilization chamber whereby substantially all air that enters the sterilization chamber passes first through the filter.

4. The method of claim 3, wherein the sterilization chamber includes an air intake baffle to prevent ultraviolet light from escaping from the sterilization chamber through the air intake opening and into the room.

5. The method of claim 4, wherein the releasing of the air including the destroyed bacteria back into the room is through an air exhaust opening in the device, and wherein the sterilization chamber includes an air exhaust baffle to prevent ultraviolet light from escaping from the sterilization chamber through the air exhaust opening and into the room.

6. The method of claim 5, wherein at least one of the intake channel and exhaust channel is coated with an ultraviolet light-absorptive coating to absorb ultraviolet light incident thereon.

7. The method of claim 1, wherein the sterilization chamber has an upstream side where the air enters the sterilization chamber and a downstream side opposite the upstream side, the upstream side and downstream side being configured such that air enters the sterilization chamber from the upstream side and passes the ultraviolet light bulb a first time, reflects off the downstream side and passes the ultraviolet light bulb a second time, and exits the sterilization chamber.

8. The method of claim 7, wherein the device includes a housing having a top surface and wherein the ultraviolet light bulbs are positioned within the housing below the top surface, and the downstream side includes a downstream surface extending from the housing top surface downward and toward the ultraviolet light bulbs, wherein the downstream surface and housing top surface define a recess to receive air flowing through the sterilization chamber and to reflect the air back toward the ultraviolet light bulbs.

9. The method of claim 1, wherein the air is drawn through the device at an air flow rate that is calculated to produce at least ten air exchanges per hour in the room.

* * * * *